United States Patent
Reid

(12)
(10) Patent No.: US 8,921,305 B2
(45) Date of Patent: Dec. 30, 2014

(54) CROTOXIN ADMINISTRATION FOR CANCER TREATMENT AND PAIN RELIEF

(71) Applicant: Paul F. Reid, Plantation, FL (US)

(72) Inventor: Paul F. Reid, Plantation, FL (US)

(73) Assignee: Celtic Biotech Iowa, Inc., West Des Moines, IA (US)

( * ) Notice: Subject to any disclaimer, the term of this patent is extended or adjusted under 35 U.S.C. 154(b) by 0 days.

(21) Appl. No.: 13/747,409

(22) Filed: Jan. 22, 2013

(65) Prior Publication Data

US 2013/0129706 A1     May 23, 2013

Related U.S. Application Data

(63) Continuation of application No. 12/946,792, filed on Nov. 15, 2010, now abandoned.

(60) Provisional application No. 61/261,333, filed on Nov. 14, 2009.

(51) Int. Cl.
| | |
|---|---|
| *A61K 38/00* | (2006.01) |
| *C07K 7/06* | (2006.01) |
| *A61K 38/46* | (2006.01) |

(52) U.S. Cl.
CPC ....... *C12Y 301/01004* (2013.01); *A61K 38/465* (2013.01)
USPC .......... 514/1.1; 514/18.3; 514/18.4; 514/19.3

(58) Field of Classification Search
None
See application file for complete search history.

(56) References Cited

U.S. PATENT DOCUMENTS 5,252,213 A * 10/1993 Ahmad et al. ................ 210/542
2007/0148159 A1 * 6/2007 Reid et al. ................ 424/94.64

OTHER PUBLICATIONS

Andren-Sandberg et al. (Annals of Oncology, 1999) Suppl 4, s265-s268.*

* cited by examiner

*Primary Examiner* — James H Alstrum Acevedo
*Assistant Examiner* — Li Lee
(74) *Attorney, Agent, or Firm* — Davis, Brown, Koehn, Shors & Roberts, P.C.

(57) ABSTRACT

Disclosed is a method for treating cancer and/or pain using an intra-patient dose escalation procedure to deliver dosages of crotoxin.

14 Claims, No Drawings

CROTOXIN ADMINISTRATION FOR CANCER TREATMENT AND PAIN RELIEF

CROSS-REFERENCE TO RELATED APPLICATIONS

This application claims the benefit of priority of U.S. patent application Ser. No. 12/946,792, filed Nov. 15, 2010, which claimed the benefit of priority of U.S. Provisional Patent Application No. 61/261,333, filed Nov. 14, 2009 and is incorporated herein by reference in its entirety.

FIELD OF THE INVENTION

The invention relates to compositions and methods for the treatment of cancer. More specifically, the invention relates to compositions comprising snake venoms and methods for their safe administration for cancer treatment.

BACKGROUND OF THE INVENTION

In 2005, 7.6 million people worldwide died of cancer. Based on projections, cancer deaths will continue to rise with an estimated 9 million people dying from cancer in 2015, and 11.4 million dying in 2030. Each year in the European Union (EU) countries, nearly two million people are diagnosed with cancer and there are over one million deaths from the disease (Cancer Research UK). It is estimated that there are nearly three million people alive in the EU who have received a diagnosis of cancer in the last five years (Cancer Research UK).

There are over 50 drugs used in cancer treatment, but many of these drugs have an average efficacy of about 20% and produce significant side effects. Cancer patients often forego treatment in order to avoid the decreased quality of life associated with side effects such as nausea, vomiting, loss of appetite, weight loss, generalized weakness, and hair loss. In fact, there is a significant demand for drugs that counteract the side-effects of anti-cancer therapy (e.g., Procrit®).

Snake venoms have demonstrated cytotoxic activity on tumour cell lines in vitro, although their anticancer properties in animal models have been studied only in a limited manner. The venoms from cobras contain large amount of basic, non-enzymatic peptides of molecular weight 6.8 kDa, generically called Cardiotoxin, which display cytolytic activity on a broad variety of tumor cells, and to a lesser extent, normal cells. Crotoxin, isolated from the venom of the South American rattlesnake, *Crotalus durissus* terrificus, has proven to have significant and broad acting anti-tumour activity both in-vitro and in-vivo. Its increased affinity for cancer cells is due primarily to the target subunit (A, crotapotin) and cell death is brought about by the B subunit (Crotactine) through the membrane-disrupting enzymatic activity. It has significant potential as a therapeutic agent, but it also has significant neurotoxic activity. Crotoxin, however, induces tolerance to its neurotoxic effects without altering the cytolytic properties, permitting the use of doses above that which would normally be lethal to the host. Mice injected daily with progressively increasing doses of Crotoxin develop tolerance to the lethal action of the toxin. Treated mice tolerated daily doses of Crotoxin 20 to 35 fold higher than the original LD50, without the characteristic signs of toxicity. It has a significantly higher lethal activity toward cancerous cells than normal cells, and this effect has been presumed to be due to the altered make-up of the cell membranes produced by rapidly proliferating cells. The sensitivity of cancer cells to Crotoxin has been associated with their expression of epidermal growth factor, a surface receptor associated with malignancy. Cancer cell lines with the highest sensitivity to Crotoxin include lung, CNS, and melanoma.

Crotoxin has been used in several human safety studies alone and in combination with Cardiotoxin (a combination of Crotoxin and Cardiotoxin in 1:1 ratio is known as VRCTC310) in patients with refractory cancer. Crotoxin, administered by intramuscular injection, was well tolerated when administered alone or in combination with Cardiotoxin, with a maximum tolerable dose (MTD) of 0.21 mg/m$^2$. Upon intramuscular injection Crotoxin achieves maximal circulating levels at 1 hour and is effectively cleared within 24 hours. Several severely ill patients have been reported to respond to treatment with reduced tumor burden, amelioration of pain, and improved quality of life. Given intramuscularly, Crotoxin gives objective clinical responses in doses close to the maximum tolerated dose (MTD). Preclinical animal data suggests that, by using a dose escalation protocol, the administration of very high doses can be achieved without adverse toxicity because the host becomes tolerant to the neurotoxic effects.

To date, subjects treated with Crotoxin have an overall response rate of 43% in a variety of tumour types. When compared to current biologic therapies, Crotoxin appears to be almost twice as active as its nearest competitor. While many other biologic therapies must be combined with conventional treatments and only serve to extend survival by marginal amounts, Crotoxin is a monotherapy, and has demonstrated sufficient activity to results in complete remissions in a relatively high percentage of terminally ill subjects under protocols that have not yet been optimized. It appears that Crotoxin has its highest cytocidal activity against highly malignant cancers, yet the side-effect profile is quite mild in comparison to other forms of chemotherapy or radiotherapy. Side-effects (e.g., diplopia, strabismus, ptosis, peripheral blockade of neuromuscular transmission) do exist, however, and have been reported in dose tolerance studies (Cura, J. et al., "Phase I and Pharmacokinetics Study of Crotoxin (Cytotoxic PLA2, NSC-624244) in Patients with Advanced Cancer," Clinical Cancer Research, Vol. 8, April 2002, p. 1033-1041).

What would be of great benefit, would be the development of methods for optimizing higher dosage levels of Crotoxin while minimizing the neurotoxic side-effects.

SUMMARY OF THE INVENTION

The invention relates to Crotoxin compositions for intravenous administration and dosing regimens for administering those compositions to provide a cytotoxic effect on cancer cells and tumors without associated neurotoxic side-effects. Compositions of the invention comprise Crotoxin doses of from about 0.04 to about 0.32 mg/m$^2$ (about 0.0012 to about 0.01 mg/Kg) suitable for intravenous administration using an intra-patient dose escalation procedure. The invention also comprises a method for treating cancer comprising administering to a cancer patient a dosage of from about 0.04 to about 0.32 mg/m$^2$ (0.0012 to 0.01 mg/Kg), the dosage being intravenously administered in an intra-patient dose escalation procedure, the intra-patient dose escalation procedure comprising administering sequentially about 0.04 mg/m$^2$/day for a period of 3-5 days, about 0.12 mg/m$^2$/day for a period of 3-5 days, about 0.16 mg/m$^2$/day for a period of 3-5 days, about 0.20 mg/m$^2$/day for a period of 3-5 days, about 0.24 mg/m$^2$/day for a period of 3-5 days, about 0.28 mg/m$^2$/day for a period of 3-5 days, and about 0.32 mg/m$^2$/day for a period of 3-5 days. In some aspects, the procedure may further comprise a two-day non-treatment period between each 3- to 5-day treatment period. In some aspects, the procedure may also comprise administration by saline drip over a two-hour period.

The invention also relates to methods of use of Crotoxin comprising intra-patient dose escalation of Crotoxin injections for the treatment of pain and/or for the treatment of neurologic and/or neuromuscular disorders. Pain may be associated with cancer, with arthritis, with multiple sclerosis, or any of a variety of sources of pain. In one aspect, the intra-patient dose escalation protocol is effective for the alleviation of pain associated with pancreatic cancer.

The invention also relates to methods of use of Crotoxin injections provided in an intra-patient dose escalation protocol in conjunction with the administration of aspirin (acetylsalicylic acid) for the alleviation of pain.

DETAILED DESCRIPTION

The inventors have developed an intra-patient dose escalation procedure for intravenous administration of Crotoxin for the treatment of cancer. The method may also be used for administration of Crotoxin for the treatment of pain and for the treatment of diseases associated with autoimmunity and inflammation. In the procedure, Crotoxin doses of from about 0.04 to about 0.32 mg/m$^2$ (0.0012 to 0.01 mg/Kg) are administered daily by intravenous administration over a 2-hour period by saline drip. The definition of DLT (dose-limiting toxicity) in the context of this procedure is described as inability of a patient to tolerate dose escalation twice. Should Crotoxin-related toxicity occur, as evidenced by neurological side-effects resulting from peripheral blockade of neuromuscular transmission, a patient is given the previous dose for another cycle (3-5 days), and upon completion of the repeated cycle, 2nd dose escalation is attempted. If the patient responds with Crotoxin-related toxicity after the $2^{nd}$ dose escalation attempt, the escalation is abandoned for this patient and the dose to which escalation was made is assessed as DLT for this patient. The patient is allowed to remain on the highest tolerated dose for another 4 weeks, subject to clinical assessment from the treating physician. After 4 weeks, tumor assessment is performed to assess potential efficacy of the dosage. Example dosing regimens are shown in Tables 1 and 2.

Briefly the method for treating cancer comprises administering to a cancer patient at least one Crotoxin dosage of from about 0.04 to about 0.32 mg/m$^2$, the dosage being intravenously administered in an intra-patient dose escalation procedure, the intra-patient dose escalation procedure comprising consecutive administration of about 0.04 mg/m$^2$/day for a 3-5 day treatment period, about 0.12 mg/m$^2$/day for a 3-5 day treatment period, about 0.16 mg/m$^2$/day for a 3-5 day treatment period, about 0.20 mg/m$^2$/day for a 3-5 day treatment period, about 0.24 mg/m$^2$/day for a 3-5 day treatment period, 0.28 mg/m$^2$/day for a 3-5 day treatment period, and 0.32 mg/m$^2$/day for a 3-5 day treatment period, wherein each successive dose escalation is conditioned upon the absence of dose-limiting toxicity from the previous dose. The intra-patient dose escalation procedure may include a two-day non-treatment period between each treatment period. For example, treatment may be performed during weekdays (i.e., Monday through Friday), with a break from treatment on the weekend.

The dosage provided in the method may be, for example, administered intravenously, such as by saline drip. In one aspect, administration may be performed by intravenous saline drip over about a two hour period.

The invention also provides a method for treating pain in a patient comprising administering to the patient at least one Crotoxin dosage of from about 0.04 to about 0.32 mg/m$^2$, the dosage being intravenously administered in an intra-patient dose escalation procedure, the intra-patient dose escalation procedure comprising consecutive administration of about 0.04 mg/m$^2$/day for a 3-5 day treatment period, about 0.12 mg/m$^2$/day for a 3-5 day treatment period, about 0.16 mg/m$^2$/day for a 3-5 day treatment period, about 0.20 mg/m$^2$/day for a 3-5 day treatment period, about 0.24 mg/m$^2$/day for a 3-5 day treatment period, 0.28 mg/m$^2$/day for a 3-5 day treatment period, and 0.32 mg/m$^2$/day for a 3-5 day treatment period, wherein each successive dose escalation is conditioned upon the absence of dose-limiting toxicity from the previous dose. In various aspects, the pain may be associated with cancer, arthritis, multiple sclerosis, and/or other disease conditions which are associated with pain. In certain aspects, the pain may be associated with pancreatic cancer, which has been described to be a particularly painful condition, with pain at later stages of the disease being refractory to many forms of pain relief.

TABLE 1

Dosing Regimen #1

| Dose Level | CROTOXIN Daily Dose | Days (starting Monday), no treatment on weekends | Duration In days |
|---|---|---|---|
| 1 | 0.04 mg/m$^2$/day | 1-5 | 5 |
| 2 | 0.08 mg/m$^2$/day | 8-12 | 5 |
| 3 | 0.12 mg/m$^2$/day | 15-19 | 5 |
| 4 | 0.16 mg/m$^2$/day | 22-26 | 5 |
| 5 | 0.20 mg/m$^2$/day | 29-33 | 5 |
| 6 | 0.24 mg/m$^2$/day | 36-40 | 5 |
| 7 | 0.28 mg/m$^2$/day | 43-47 | 5 |
| 8 | 0.32 mg/m$^2$/day | 50-54 | 5 |

TABLE 2

Dosing Regimen #2

| Dose Level | CROTOXIN Daily Dose | Days (starting Monday), no treatment on weekends | Duration In days |
|---|---|---|---|
| 1 | 0.04 mg/m$^2$/day | 1-3 | 3 |
| 2 | 0.08 mg/m$^2$/day | 4-5, 8-10 | 5 |
| 3 | 0.12 mg/m$^2$/day | 11-12, 15 | 3 |
| 4 | 0.16 mg/m$^2$/day | 16-18 | 3 |
| 5 | 0.20 mg/m$^2$/day | 19, 22-24 | 4 |
| 6 | 0.24 mg/m$^2$/day | 25-26, 29 | 3 |
| 7 | 0.28 mg/m$^2$/day | 30-32 | 3 |
| 8 | 0.32 mg/m$^2$/day | 33, 36-37 | 3 |

For the treatment of pain, an intra-patient dose escalation protocol may comprise intravenous administration as provided in Table 1 and/or Table 2, or may comprise Crotoxin injection with or without the administration of aspirin, in a dosing regimen comprising a minimal dose of about 0.05 cc or about 0.1 cc given for a period of 5 days, followed by incremental increases in dosage administered for similar periods of time (e.g., 3-5 days). Diphenhydramine (e.g., Benadryl®) may also be pre-administered or co-administered to minimize a reaction to the Crotoxin.

The invention may be further described by means of the following non-limiting examples.

EXAMPLES

Multi-Patient 2-Cohort Study:

Individuals selected for the study are adult patients with histologically confirmed advanced solid tumors who have progressed despite standard therapy, or for whom no standard therapy exists; have an ambulatory PS (ECOG 0-1); have tumour evaluation made within 28 days before study drug administration (patients with non-measurable lesions according to the RECIST guidelines not previously irradiated are allowed to enter the trial); have completed radiotherapy or chemotherapy or any other anticancer therapy (including experimental therapy) more than 4 weeks prior to enrollment into the trial and must have recovered from all acute side effects of these treatments; have a life expectancy greater than 3 months; have an age between 18 and 75 years; have normal marrow function with normal haematological parameters (Hb$\geq$10 g/dl, WBC$\geq$4.0$\times$10$^9$/L, neutrophil count$\geq$2.0$\times$10$^9$/L and platelets$\geq$100$\times$10$^9$/L); have no medically significant impairment of cardiac or respiratory functions; have adequate hepatic function with total bilirubin$\leq$1.5$\times$N and transaminases$\leq$2.5$\times$N ($\leq$5$\times$N in case of liver metastasis); have no history of prior severe allergic reactions to venoms; have creatinine clearance$\geq$50 mL/min.

Additionally, patients must already be on stable doses of any drugs which may affect hepatic drug metabolism or renal drug excretion (e.g., non-steroidal anti-inflammatory drugs, barbiturates, narcotic analgesics, probenecid), they should not be pregnant or planning to become pregnant, should not be known to have brain metastases or leptomeningeal involvement (CT-scan or MRI is not required to rule this out unless there is clinical suspicion of central nervous system involvement), should not have pleural effusion/ascites, cystic lesions or bone metastases, should not be receiving any other experimental or anti-cancer therapy within 30 days before first study drug administration (except antalgic radiotherapy and hormonotherapy), should not have a history of other malignancies (except for patients with a cancer free interval of greater than or equal to 5 years after treatment completion or patients with prior history of adequately treated basal cell carcinoma of the skin or carcinoma in situ of the cervix), should not have had recent major surgery (within 21 days) should not have a recent history of weight loss greater than 10% of current body weight, should not have serious intermittent medical illnesses which would interfere with the ability of the patient to carry out the treatment program, should not be on chronic steroid medication (greater than 20 mg/day), and should not have primary or paraneoplastic myasthenia gravis.

Crotoxin doses of about 0.04 to 0.32 mg/m$^2$ (0.0012 to 0.01 mg/Kg) are administered using an intra-patient dose escalation procedure. The definition of DLT (dose-limiting toxicity) in the context of this study is described as inability of dose escalation twice. Should Crotoxin-related toxicity occur, the patient is given the previous dose for another cycle (5 days) upon which 2$^{nd}$ dose escalation is attempted. If the patient responds with drug treatment related Crotoxin-related toxicity after the 2$^{nd}$ dose escalation attempt, the escalation is abandoned for this patient and the dose to which escalation was made is assessed as DLT for this patient. The patient is offered to remain on the highest tolerated dose for another 4 weeks, subject to clinical assessment from the treating physician. After 4 weeks, tumor assessment is performed to assess potential efficacy of the tested compound.

Determination of general MTD may be done as follows: first, a patient is treated up to a 0.32 mg/m$^2$ or a lower tolerated dose. This dose is called the i$^{th}$ target ceiling dose (TCD$_i$). Next, two patients will be treated up to the TCD$_i$. If no Crotoxin-related toxicity (dose-limiting toxicity, DLT) is encountered at the TCD$_i$, then the TCD$_i$ is the MTD. If two or more DLT are encountered, then 3 new patients are included to receive the next lower dose (TCD$_{i-1}$), etc. If one DLT is encountered, then 3 more patients are added to receive dosages up to the TCD$_i$. If no DLT is encountered among those 3 new patients, then the TCD$_i$ is MTD. If one or more DLT is encountered among those 3 new patients, then 3 new patients are included up to TCD$_{i-1}$, etc.

Crotoxin is administered daily by intravenous administration over a 2-hour period by saline drip. Each patient will receive Ranitidine 50 mg (antiemetic) and Polaramine® 10 mg I.V. 10 mg (antihistamine) intravenously prior to treatment to minimize the potential for anaphylaxis.

Patients are treated as out-patients, attending the clinic daily for treatment, monitored at the clinic for the duration of the infusion (2 hours), and observed for 30 minutes following the infusion of the drug. If adverse events are to occur (anaphylaxis or neurotoxicity), they are expected to manifest themselves during the administration of the drug allowing interruption of treatment (stopping of the infusion) as circulating levels of the drug will rapidly fall once administration has ceased. The procedure to suppress the potential for anaphylaxis is followed in a standard protocol employed for any agent that can induce hypersensitivity reaction (e.g., such procedures are employed when administering Radio Contrast Media and monoclonal antibody therapies such as trastuzumab or cetuximab).

Crotoxin Administration Alleviates Pain Related to Pancreatic Cancer and Multiple Sclerosis A female patient with both pancreatic cancer and multiple sclerosis experienced such pain that it was not alleviated by medications such as hydromorphone and/or fentanyl. She began a dose escalation protocol comprising injectable Crotoxin starting at 0.01 cc. A dose of 0.1 cc contains 40 micrograms Crotoxin or about 0.6 micrograms/kilogram. She has been maintained at the 0.1 cc dose and reports being pain free and able to move muscles and joints without experiencing pain. Of even more significance, she reports experiencing no pancreatic pain. The decrease in pain was of such magnitude that the patient experienced it as a sense of euphoria.

What is claimed is:

1. A method for treating cancer comprising:
   administering to a cancer patient at least one Crotoxin dosage of from about 0.04 to about 0.32 mg/m$^2$, the dosage being intravenously administered in an intra-patient dose escalation procedure, the intra-patient dose escalation procedure comprising consecutive administration of:
   about 0.04 mg/m$^2$/day for a 3-5 day treatment period;
   about 0.12 mg/m$^2$/day for a 3-5 day treatment period;
   about 0.16 mg/m$^2$/day for a 3-5 day treatment period;
   about 0.20 mg/m$^2$/day for a 3-5 day treatment period;
   about 0.24 mg/m$^2$/day for a 3-5 day treatment period;
   about 0.28 mg/m$^2$/day for a 3-5 day treatment period;
   and about 0.32 mg/m$^2$/day for a 3-5 day treatment period;
   wherein each dose is co-administered with an antihistamine; and wherein each successive dose escalation is conditioned upon the absence of dose-limiting toxicity from the previous dose.

2. The method of claim 1 wherein the intra-patient dose escalation procedure further comprises a two-day non-treatment period between each treatment period.

3. The method of claim 1 wherein the dosage is intravenously administered by saline drip.

4. A method for treating pain in a patient comprising:
administering to the patient at least one Crotoxin dosage of from about 0.04 to about 0.32 mg/m$^2$, the dosage being intravenously administered in an intra-patient dose escalation procedure, the intra-patient dose escalation procedure comprising consecutive administration of;
about 0.04 mg/m$^2$/day for a 3-5 day treatment period;
about 0.12 mg/m$^2$/day for a 3-5 day treatment period;
about 0.16 mg/m$^2$/day for a 3-5 day treatment period;
about 0.20 mg/m$^2$/day for a 3-5 day treatment period;
about 0.24 mg/m$^2$/day for a 3-5 day treatment period;
about 0.28 mg/m$^2$/day for a 3-5 day treatment period;
and 0.32 mg/m$^2$/day for a 3-5 day treatment period;
wherein each dose of Crotoxin is co-administered with an antihistamine; and wherein each successive dose escalation is conditioned upon the absence of dose-limiting toxicity from the previous dose.

5. The method of claim 4 wherein the pain is associated with cancer.

6. The method of claim 5 wherein the cancer is pancreatic cancer.

7. The method of claim 4 wherein the pain is associated with arthritis.

8. The method of claim 4 wherein the pain is associated with multiple sclerosis.

9. The method of claim 1 wherein the antihistamine is administered intravenously.

10. The method of claim 1 wherein each dose of Crotoxin is co-administered with an antiemetic.

11. The method of claim 10 wherein the antiemetic is administered at a dose of about 50 mg.

12. The method of claim 4 wherein the antihistamine is administered intravenously.

13. The method of claim 4 wherein each dose of Crotoxin is co-administered with an antiemetic.

14. The method of claim 13 wherein the antiemetic is administered at a dose of about 50 mg.

* * * * *